US00PP25933P3

(12) United States Plant Patent
Hill

(10) Patent No.: US PP25,933 P3
(45) Date of Patent: Sep. 22, 2015

(54) ***VRIESEA* PLANT NAMED 'V807-1'**

(50) Latin Name: ***Vriesea* hybrid**
Varietal Denomination: V807-1

(71) Applicant: Herb Hill, Lithia, FL (US)

(72) Inventor: Herb Hill, Lithia, FL (US)

(73) Assignee: 3B Fundus B.U. (NL)

( * ) Notice: Subject to any disclaimer, the term of this patent is extended or adjusted under 35 U.S.C. 154(b) by 165 days.

(21) Appl. No.: 13/998,394

(22) Filed: Oct. 28, 2013

(65) Prior Publication Data

US 2015/0121589 P1 Apr. 30, 2015

(51) Int. Cl.
*A01H 5/02* (2006.01)

(52) U.S. Cl.
USPC ..... Plt./370

(58) Field of Classification Search
USPC ..... Plt./370
See application file for complete search history.

*Primary Examiner* — Anne Grunberg
(74) *Attorney, Agent, or Firm* — Cassandra Bright

(57) ABSTRACT

A new and distinct *Vriesea* cultivar named 'V807-1' is disclosed, characterized by a thick inflorescence colored bright yellow with an orange base. The new variety is a *Vriesea,* typically produced as an indoor ornamental plant.

1 Drawing Sheet

Latin name of the genus and species: *Vriesea* hybrid.
Variety denomination: 'V807-1'.

BACKGROUND OF THE INVENTION

This application relates to a new cultivar of *Vriesea*. The new variety is the product of a planned breeding program. The new variety originated as a seedling from the crossing of the unpatented, proprietary seed parent *Vriesea* 'V402-1' with the unpatented, proprietary pollen parent referred to as *Vriesea* 'V666-1'. The crossing was made by the inventor in his research greenhouse in Lithia, Fla. in March of 2003.

The new variety was first selected by the inventor, Herb Hill, a citizen of United States, in April of 2006 in a research greenhouse belonging to the inventor in Lithia, Fla. After identifying the new variety as a potentially interesting selection, the inventor continued confidential testing and propagation of 'V807-1', assessing stability of the unique characteristics of this variety.

Asexual reproduction of the new cultivar 'V807-1' was first performed at a commercial laboratory in Kudelstaart, Netherlands by tissue culture in 2008. Access to all plants was restricted, as plants were kept in a greenhouse not open to the public. Through subsequent propagation, multiple generations have been reproduced, which have shown that the unique features of this cultivar are stable and reproduced true to type.

SUMMARY OF THE INVENTION

The cultivar 'V807-1' has not been observed under all possible environmental conditions. The phenotype may vary somewhat with variations in environment such as temperature, day length, and light intensity, without, however, any variance in genotype.

The following traits have been repeatedly observed and are determined to be the unique characteristics of 'V807-1.' These characteristics in combination distinguish 'V807-1' as a new and distinct *Vriesea* cultivar:

1. Bright yellow inflorescence with orange base.
2. Green leaves.
3. Wide inflorescence.

PARENT COMPARISON

Plants of the new cultivar 'V807-1' are similar to the seed parent, *Vriesea* 'V402-1' in most horticultural characteristics. However the new variety, 'V807-1' differs from 'V402-1' in the following characteristics:

1. Yellow inflorescence whereas seed parent's inflorescence is orange.

Plants of the new cultivar 'V807-1' are similar to the pollen parent, *Vriesea* 'V666-1' in most horticultural characteristics. However the new variety, 'V807-1' differs from 'V666-1' in the following characteristics:

1. Different shade of yellow inflorescence.

COMMERCIAL COMPARISON

'V807-1' is similar in most horticultural characteristics to the unpatented commercial variety *Vriesea* 'Evita' in most horticultural characteristics. However the new variety, 'V807-1' differs from 'Evita' in the following characteristics:

1. Thicker more intensely colored inflorescence than comparator.
2. Broader leaves than comparator.

BRIEF DESCRIPTION OF THE PHOTOGRAPH

The accompanying photograph in FIG. 1 illustrates in full color a typical plant of 'V807-1' grown in a commercial greenhouse in De Kwakel, Netherlands.

The plant is 20 months old from a rooted cutting, in a 12 cm pot. The photograph was taken using conventional techniques and although colors may appear different from actual colors due to light reflectance it is as accurate as possible by conventional photographic techniques.

DETAILED BOTANICAL DESCRIPTION

In the following description, color references are made to The Royal Horticultural Society Colour Chart 2007, except where general terms of ordinary dictionary significance are used. The following observations and measurements describe a typical plant of 'V807-1' grown in a commercial greenhouse in De Kwakel, Netherlands. The plant is 20 months old from a rooted cutting, in a 12 cm pot. Temperatures ranged between 20° C. and 28° C. during the day 18° C. and 22° C. at night. Measurements and numerical values represent averages of typical plant types.

Botanical classification: *Vriesea* hybrid 'V807-1'.

PROPAGATION

Type of propagation typically used: Tissue culture.

Time to initiate roots: About 15 days at approximately 20° C.

Time to produce a rooted cutting/liner: About 180 days at approximately 22° C.

Root description: Densely branched, non-fibrous, non-fleshy, colored Greyed-orange; near RHS 165A.

PLANT

Growth habit: Main rosette with inflorescence growing from the centre; overall plant-shape: broad ovate.

Height: Approximately: 41.8 cm.

Plant spread: Approximately: 45.0 cm.

Normal pot size: 12 cm circular pot.

Growth rate: Moderate.

Branching characteristics: No stems, no lateral branches present, plant consists of a basal rosette.

Number of leaves per stem: Approximate number of leaves per rosette (no stems present): 25.

FOLIAGE

Leaf:

*Arrangement.*—Rosulate (in a basal rosette).

*Average length.*—Approximately 26.5 cm.

*Average width.*—Approximately 4.7 cm (measured at 50% of the leaf blade).

*Shape of blade.*—Ligulate.

*Aspect.*—Leaves in an average angle of 55° to horizontal (=0°).

*Apex.*—Abruptly acute, moderately twisted, tip slightly to moderately downward in an average angle of −80° to horizontal (=0°).

*Base.*—Decurrent. Sheath length: Average 8.2 cm. Sheath width: Average 7.5 cm. Sheath color: Upper side yellow-green; near RHS 148B, tinged purple; near RHS N77C, under side greyed-purple; near RHS 187B.

*Margin.*—Entire.

*Texture of top surface.*—Smooth, very glossy.

*Texture of bottom surface.*—Smooth, very glossy.

*Color.*—Young foliage upper side: Green to yellow-green; in between RHS 143A and 146A. Young foliage under side: Green; near RHS 143C, apex yellow-green; near RHS 146A. Mature foliage upper side: Yellow-green; near RHS 147A but much darker, strongly tinged brown; near RHS 200B. Mature foliage under side: Yellow-green; near RHS 148A, moderately to strongly tinged greyed-purple; near RHS 187A.

*Venation.*—Type: Parallel. Venation coloration: As leaf blade.

Petiole: No petiole present.

INFLORESCENCE

General description: Scape growing from the centre of the basal rosette, inflorescence branched into a paniculate shape; only bracts visible, individual flowers not visible but fully enclosed by bracts.

*Inflorescence height, excluding scape.*—Approximately 27.5 cm.

*Inflorescence width.*—Approximately 10.9 cm.

Scape:

*Length.*—Approximately 28.3 cm.

*Width.*—Approximately 0.8 cm.

*Aspect.*—Approximately 90° angle to rosette.

*Strength.*—Strong.

*Color.*—Yellow-green; near RHS 150D (completely covered by scape bracts).

Bracts:

*Scape/lowermost bracts.*—Shape: Ovate. Length: Approximately 2.7 cm, excluding sheath. Width: Approximately 2.6 cm (measured at the base, just above the sheath). Quantity: Average 10. Tip: Abruptly acute. Base: Sheathing. Sheath length: Approximately 3.6 cm. Sheath width: Approximately 3.2 cm. Sheath color: Greyed-purple; near RHS 185D. Margin: Entire. Color Upper side: Yellow-green; near RHS 146B, apex greyed-purple; near 187A. Color Under side: Greyed-purple to brown; in between 187A and 200B, apex greyed-purple; near N186C.

*Terminal bracts.*—Shape: Ovate, folded (flattened). Length: Approximately 3.0 cm, excluding sheath. Width: Approximately 3.6 cm; however, bracts are folded, so in effect it is two times 1.8 cm. Quantity: Average 140. Tip: Apiculate. Base: Sheathing. Sheath length: Approximately 2.0 cm. Sheath width: Approximately 3.2 cm; however, bracts are folded, so in effect it is two times 1.6 cm. Sheath color: Red; near RHS 45C to 45D. Margin: Entire. Coloration Terminal Bracts: Upper side: Yellow; near RHS 12A and 13A. Under side: Yellow-orange; near RHS 14C.

FLOWER

Flowering characteristics: Individual flowers fully enclosed by the bracts and therefore not visible from outside; each bract encloses one individual flower.

Days to flowering from tissue culture: 2 to 2.5 years.

Inflorescence and flower type and habit: Inflorescence paniculate, individual flower single.

Flower longevity on plant: Average: 3 months.

Quantity of buds and flowers per plant: Average: 140.

Persistent or self-cleaning: Persistent.

Bud:

*Shape.*—Lanceolate.

*Length.*—Average: 1.5 cm.

*Diameter.*—Average: 0.4 cm.

*Color.*—Yellow-green; near RHS 150B to 150C.

Flower size:

*Diameter.*—Average: 0.6 cm.

*Depth.*—Average: 3.1 cm.

Petals:

*Quantity.*—Average: 3.

*Arrangement.*—Rotate, fused.

*Length.*—Average: 1.4 cm.
*Width.*—Average: 0.5 cm.
*Shape.*—Oblong.
*Apex.*—Obtuse.
*Base.*—Broad cuneate, fused.
*Margin.*—Entire.
*Texture, upper and lower surfaces.*—Glabrous, moderately glossy.
*Color.*—When opening, upper surface: Yellow; near RHS 4D, tip yellow-green; near RHS 150B. When opening, lower surface: Yellow; near RHS 5D, tip yellow-green; near RHS N144A. Fully opened, upper surface: Yellow; near RHS 4D, tip yellow-green; near RHS 150B. Fully opened, lower surface: Yellow; near RHS 5D, tip yellow-green; near RHS N144A.

Sepals:
*Quantity.*—Average: 3.
*Length.*—Average: 2.6 cm.
*Width.*—Average: 1.0 cm.
*Shape* (*overall*).—Lanceolate. Apex: Acute. Base: Cuneate, fused.
*Margin.*—Entire.
*Color.*—Yellow; near RHS 10A to 10B.

Peduncles:
*Length.*—Average: 9.3 cm.
*Diameter.*—Peduncles flattened; average diameter at widest: 0.8 cm, average diameter at narrowest: 0.5 cm.
*Angle.*—About 30° to the lateral branch.
*Strength.*—Strong.
*Texture.*—Glabrous, glossy.
*Color.*—Yellow-green; near RHS 150D Fragrance: No fragrance. .

REPRODUCTIVE ORGANS

Stamens:
*Number.*—Average: 6.

Anthers:
*Shape.*—Narrow oblong.
*Length.*—Approximately 0.7 cm.
*Color.*—Yellow to yellow-orange; near RHS 13B and 14B.
*Pollen.*—No pollen detected.

Pistil:
*Number.*—Average: 1.
*Length.*—Average: 0.65 cm.
*Style.*—Length: Average: 0.6 cm. Color: Yellow-green; near RHS 150D, top darker; near RHS 151B.
*Stigma.*—Shape: Club-shaped. Color: Yellow-green; near RHS 150B to 150C. Ovary Color: Yellow-green; near RHS 150D.

OTHER CHARACTERISTICS

Disease resistance: Neither resistance nor susceptibility to the normal diseases and pests of *Vriesea* has been observed.

Temperature tolerance: Observed to tolerate temperatures to 35° C. without any negative effects. Temperature tolerance above this range has not been observed. Tolerance of cold temperatures has not been observed.

Fruit/seed production: No fruits/seeds detected to date.

What is claimed is:

1. A new and distinct cultivar of *Vriesea* plant named 'V807-1' as herein illustrated and described.

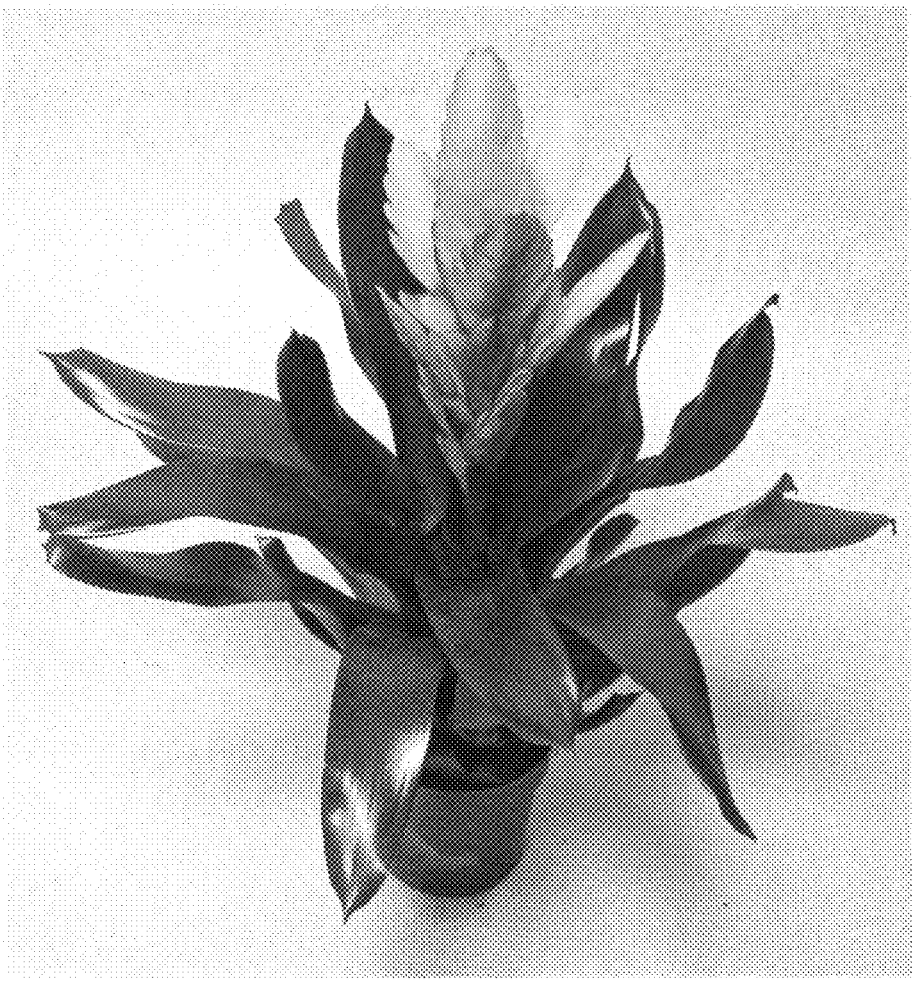

* * * * *